United States Patent [19]

Howard

[11] 4,044,007

[45] Aug. 23, 1977

[54] STABILIZATION OF BIOCIDAL COMPOSITION

[75] Inventor: William L. Howard, Lake Jackson, Tex.

[73] Assignee: The Dow Chemical Company, Midland, Mich.

[21] Appl. No.: 742,825

[22] Filed: Nov. 18, 1976

Related U.S. Application Data

[63] Continuation-in-part of Ser. No. 591,201, June 27, 1975, abandoned, which is a continuation of Ser. No. 869,902, Oct. 27, 1969, abandoned.

[51] Int. Cl.² .......................................... C07D 295/02
[52] U.S. Cl. ................................................. 544/185
[58] Field of Search ..................................... 260/248.5

[56] References Cited

U.S. PATENT DOCUMENTS

| | | | |
|---|---|---|---|
| 3,228,829 | 1/1966 | Wolf et al. | 260/248.5 X |
| 3,758,464 | 9/1973 | Prindle et al. | 260/248.5 |

*Primary Examiner*—John M. Ford
*Attorney, Agent, or Firm*—Theodore Post; C. Kenneth Bjork

[57] ABSTRACT

Adducts of certain unsaturated halides with hexamethylenetetramine are known to be effective germicides when present in concentrations as low as 0.01 percent in water-containing organic mixtures. However, under certain conditions the compounds may undergo detrimental spontaneous exothermic decomposition. Blending with the adduct an additament which undergoes an endothermic change at a temperature below that at which exothermic decomposition of the adduct decomposition thereby providing a composition stabilized for packaging and/or storage.

7 Claims, No Drawings

STABILIZATION OF BIOCIDAL COMPOSITION

CROSS-REFERENCE TO RELATED APPLICATIONS

This application is a continuation-in-part of U.S. patent application Ser. No. 591,201, filed June 27, 1975 now abandoned, which in turn is a continuation of U.S. patent application Ser. No. 869,902, filed Oct. 27, 1969 and now abandoned.

BACKGROUND OF THE INVENTION

Adducts of certain unsaturated olefinic or acetylenic halides with hexamethylenetetramine are effective germicides when present in concentrations as low as 0.01 percent in water-containing organic mixtures such as, for example, emulsified cutting oils, latexes, latex paints, aqueous adhesives, hydraulic fluids and pulp dispersions used in paper-making. The adducts, the mode of their preparation, and their utility are taught in U.S. Pat. No. 3,228,829.

In particular, as disclosed in U.S. Pat. No. 3,228,829, adducts formed by the reaction of hexamethylenetetramine with an olefinically or acetylenically unsaturated bromide, chloride, or iodide wherein the halide molecule contains a maximum of about eight carbon atoms, exhibit the antimicrobial activity of the unsaturated halide moiety as well as other valuable properties not exhibited by the unsaturated halide.

Unsaturated halohydrocarbons which form adducts with hexamethylenetetramine having particularly high antimicrobial activity are dihaloalkenes and haloalkynes such as propargyl bromide, propargyl chloride, 1,3-dichloropropene, 2,3-dichloropropene, diiodoacetylene and 1,4-dichloro-2-butyne.

The hexamethylenetetramine:unsaturated aliphatic halide adducts are prepared easily by mixing together the proper amounts of the two reactants in a suitable solvent at or about room temperature. Solvents mentioned in the literature as suitable for use in this general reaction include, for example, dichloromethane, chloroform, methanol and ethanol.

Although, as set forth hereinbefore, these adducts are very effective antimicrobials, under certain conditions it has been found that the compounds may undergo spontaneous exothermic decomposition. This phenomenon, if it occurs, has arisen usually in those instances where the mass of a substantially water-free adduct is such that there is inadequate means for heat transfer from the interior of the mass to the surrounding environment. Generally, such sporadic spontaneous decomposition has been found to occur where packages or large compact piles of the substantially water-free compound have been stored or accumulated, such as commonly practiced in the warehousing or other inventory storage of materials. Heretofore, means for providing heat transfer to eliminate or suppress the decomposition primarily have been directed to limiting the size of the mass of the substantially water-free biocidal adduct in at least one dimension to provide a short heat transfer path which prevents the development of a detrimentally large temperature difference between the interior of the mass and tht environment, e.g., the atmosphere and walls of a package. Conveniently, small or thin elongated shaped packages wherein large substantially water-free masses are not accumulated in a given location are suitable for storage.

Now, unexpectedly, I have found a substantially water-free composition comprising an adduct of hexamethylenetetramine with an olefinic or acetylenic halide wherein autodecomposition from spontaneous exothermic reaction is entirely prevented or suppressed to a point where there is no detrimental product degradation.

It is a principal object of the present invention to provide a substantially water-free composition comprising an adduct of hexamethylenetetramine with an olefinic or acetylenic halide which does not undergo spontaneous detrimental degradation when stored in large masses.

It is another object of the present invention to provide a substantially water-free composition wherein spontaneous exothermic decomposition of adducts of the type set forth hereinbefore can be suppressed and even eliminated, thus markedly increasing the ease of bulk storage and packaging of such adducts.

It is a further object of the present invention to provide a substantially water-free composition which is stable against autoinitiated exothermic reaction of the active antimicrobial ingredient, i.e., a 1:1 hexamethylenetetramine:unsaturated aliphatic halide adduct, but wherein the biocidal effectiveness of this active ingredient is not impaired.

It is also an object of the present invention to provide a substantially water-free composition in which such an exothermic degradation will not be self-propagating throughout a compact mass.

These and other objects and advantages readily will become apparent from the detailed description presented hereinafter.

SUMMARY OF THE INVENTION

In general, the present invention is a substantially water-free composition comprising a hexamethylenetetramine - olefinic halide adduct or hexamethylenetetramine -acetylenic halide adduct having in combination therewith an additament compound, hereinafter at times referred to as a suppressor additive, which suppressor additive undergoes an endothermic change at a temperature below that at which spontaneous exothermic decomposition of the adduct is initiated. The quantity of additament to be employed should be sufficient to provide for absorption, in its endothermic reaction, of enough of the energy from the heat of reaction released by the adduct in undergoing spontaneous exothermic decomposition to prevent the attainment of propagating temperatures in the mass. By a "substantially water-free composition" is meant a composition to which water as such has not been added.

DESCRIPTION OF SOME PREFERRED EMBODIMENTS

In a preferred embodiment of the composition of the present invention, a 1:1 adduct of hexamethylenetetramine and an olefinic or acetylenic halide is blended with a suppressor additive in an amount sufficient to eliminate or suppress any self-propagating exothermic decomposition of the adduct. The preferred additive is a polymeric form of an aliphatic aldehyde wherein the monomeric aldehyde has from 1 to 2 carbon atoms, alkali metal- or ammonium hydrogen carbonate, an alkali metal- or ammonium salt of a polycarboxylic aliphatic acid having a total of from 2 to 8 carbon atoms, or urea or its autocondensation products, e.g., biuret and triuret.

Representative additives which have been found to be particularly suitable for use in the present compositions are paraformaldehyde, sodium bicarbonate, ammonium bicarbonate, urea, ammonium citrate, biuret and s-trioxane.

The actual quantities of additive to be employed in a given composition will depend on the predetermined suppressor additive selected. Generally, from about 5 to about 90 weight percent of the additive and from about 95 to about 10 weight percent of the adduct are employed in the composition. Ordinarily, the compositions range from about 15 to about 45 weight percent of the additive and from about 85 to about 55 weight percent of the adduct. Within this range, it is to be understood that quantities of a particular additive greater than the minimum set forth or less than the maximum disclosed as required to obtain substantially complete suppression of the exothermic autodecomposition of a given adduct can be used. To illustrate, with a 1:1 adduct of hexamethylenetetramine and 1,3-dichloropropene, (i.e., 1-(3-chloroallyl) 1-azonia-3,5,7-triazoadamantane chloride) a blend containing about 5 weight percent of paraformaldehyde based on total composition has been found to suppress spontaneous exothermic decomposition of the adduct. Similarly, a composition comprising about 20 weight percent of sodium bicarbonate and 80 weight percent of the adduct exhibited no spontaneous exothermic decomposition.

Paraformaldehyde offers the additional advantage in that in its endothermic reaction it absorbs relatively large amounts of heat energy per unit of weight; also, in this change, formaldehyde is produced. This latter compound itself is biocidal. Sodium bicarbonate provides effective control at a relatively low cost. Further, in some instances, bicarbonate properties may be desired.

Compositions containing the additive in amounts greater than that disclosed provide the desired suppression of the spontaneous exothermic decomposition of the adduct, but this excess is not required. In some instances, it may be detrimental in that with unduly large quantities of additive, the adduct may be undesirably diluted, thereby requiring larger amounts of the composition than desired for a given antimicrobial application.

The composition of the present invention can be prepared by dry blending predetermined quantities of the suppressor additive and adduct to provide a substantially homogeneous composition.

Alternatively, the compositions can be formed in situ by incorporating a predetermined amount of the additive into the reaction mixture employed to prepare the adduct. In such operations, usually the additive and hexamethylenetetramine are placed in a reactor along with an inert liquid carrier to provide a mobile slurry. The resulting mixture is agitated and heated to a predetermined reaction temperature under an inert atmosphere and a predetermined amount of an unsaturated aliphatic halide adduct former controllably added thereto. Following completion of the aliphatic halide addition, the reaction mass is maintained under agitation for a period of time after which the product mass is removed from the reactor, the resulting solid adduct - additive blend composition separated from the liquid carrier, and the recovered composition dried.

The following examples will serve to further illustrate ahd present invention but are not meant to limit it thereto.

EXAMPLE 1

Sample containers were prepared by forming aluminum foil into small troughs about 2½ inches long by 7/16 inch wide and having a depth of about 1 inch. Five grams of a homogenous mixture of a 1:1 hexamethylenetetramine:1,3-dichloropropene adduct and a predetermined amount of paraformaldehyde as additive were dry blended and packed into each trough to an even depth for the full length of the trough. As a control, a similar quantity of the adduct itself was placed in one of the troughs. Each mass was subjected at one end to direct contact with an electrically heated filament of nichrome wire to provide an extreme condition as may be present during actual exothermic autodecomposition. The behavior of the composition was observed. The paraformaldehyde additive concentration for the various compositions studied and observed results are summarized in Table I.

Table I

| Run No. | Amount of Additive (wt. %)* | Results |
| --- | --- | --- |
| 1 | 0 (control) | rapid degradation, i.e. decomposition, through entire sample |
| 2 | 6 | slow propagation through sample |
| 3 | 10 | degradation proceeded slowly through a portion of the sample; stopped before reaching end |

*based on total composition weight, adduct provides the balance of the composition.

EXAMPLE 2

Aluminum foil was shaped into a trough-shaped sample container 3 inches long, about 1 inch deep and having a width of either 7/16 inch or 1 inch. A thin divider was placed at about the midpoint of each container making two compartments each about 1½ inches long. One compartment of each trough was packed with the 1:1 hexamethylenetetramine:1,3-dichloropropene adduct. The other compartment of the trough was packed with a homogeneously blended two-compartment composition of the adduct and 15 or 20 weight percent, based on the total composition weight, of paraformaldehyde. The compartment divider was withdrawn and the contents of the two compartments brought into direct, intimate contact at their interface by careful tamping. As a control, one compartment of each sized container was filled with adduct alone. A hot nichrome filament was placed into the adduct at the end of the compartment away from the interface. Behavior of the samples was followed by visual observation.

Table II summarizes the results of this study.

Table II

| Run No. | Container Width (in.) | Paraformaldehyde Concentration (Weight %) | Results |
| --- | --- | --- | --- |
| 1 | 7/16 | 0 (control) | Complete decomposition and degradation through the adduct in 30–45 seconds. |
| 2 | 7/16 | 15 | Decomposition through adduct compartment in 30–45 seconds. Reaction stopped at interface between compositions where smoking continued for about one minute and then ceased. |
| 3 | 1 | 0 (control) | Complete decomposi- |

Table II-continued

| Run No. | Container Width (in.) | Paraformaldehyde Concentration (Weight %) | Results |
|---|---|---|---|
| 4 | 1 | 15 | tion and degradation through the adduct in 30-45 seconds. Propagation decomposition was markedly retarded when it encountered the additive-containing composition; reaction proceeded slowly through the composition over a period of about 4 minutes. |
| 5 | 1 | 20 | Decomposition stopped at interface of the composition. |

EXAMPLE 3

Compositions were prepared by either dry blending or in situ preparation to provide a substantially homogeneous blend of a 1:1 hexamethylenetetramine:1,3-dichloropropene adduct and a predetermined quantity of a suppressor additive.

For the dry blended compositions, predetermined proportions of the additive and adduct were manually mixed in a closed bottle.

For the in situ preparation of the blended compositions, predetermined quantities of hexamethylenetetramine and suppressor additive along with an inert solvent, e.g., methylene chloride, were introduced into a reactor fitted with an agitator and the temperature controller. The amount of additive used was such as to provide a predetermined quantity of this moiety in the final composition. Ordinarily, solvent in an amount to give a slurry having a total solids content of about 30 weight percent was used.

The slurry was agitated and heated to about 60° C and maintained at this temperature while controllably adding 1,3-dichloropropene in a molar quantity equal to that of the hexamethylenetetramine. Following completion of the 1,3-dichloropropene addition, the agitated reaction mass was digested for a period of from about 6 to about 8 hours at 60° C. After this period, the product composition was removed from the reactor and dried at about 60° C under a reduced pressure.

The suppressor activity of each additive was determined by placing 8 grams of a given composition along a 4 inch section of an insulated trough 6 inches long. The remaining 2 inch section of the trough was loaded with 4 grams of the 1:1 hexamethylenetetramine:- 1,3-dichloropropene adduct. The tip of an electric soldering gun was inserted into the end of the section of adduct which was remote from the interface of the two samples to initiate exothermic decomposition of the adduct. The behavior of the additive composition was observed. The results of this study are summarized in Table III.

Table III

| Run No. | Additive Type | Wt. %* | Blend | Results |
|---|---|---|---|---|
| 1 | NaHCO₃ | 10 | Dry mix | Some discoloration about ½" to ¾" into additive containing composition. No propagation through composition |
| 2 | NaHCO₃ | 15 | In situ | Propagation stopped at interface. |
| 3 | NaCHO₃ | 20 | Dry mix | " |
| 4 | NaHCO₃ | 25 | In situ | " |

Table III-continued

| Run No. | Additive Type | Wt. %* | Blend | Results |
|---|---|---|---|---|
| 5 | NaHCO₃ | 35 | In situ | " |
| 6 | NaHCO₃ | 45 | In situ | " |
| 7 | NaHCO₃ | 90 | In situ | " |
| 8 | Urea | 15 | In situ | " |
| 9 | Urea | 20 | Dry mix | " |
| 10 | Urea | 25 | In situ | " |
| 11 | Urea | 90 | In situ | " |
| 12 | Biuret | 20 | Dry mix | " |
| 13 | Biuret | 25 | In situ | " |
| 14 | NH₄HCO₃ | 10 | Dry mix | " |
| 15 | NH₄HCO₃ | 20 | Dry mix | " |
| 16 | Dibasic ammonium citrate | 20 | Dry mix | " |
| 17 | s-Trioxane | 10 | Dry mix | Decomposition extended about one inch into mixture and then stopped. |
| 18 | s-Trioxane | 20 | Dry mix | Propagation stopped at interface. |

*based on total weight of composition.

The conditions for determining stability of the compositions studied in Examples 1-3 purposely were selected to be extreme, i.e., an external high temperature stimulus was employed to initiate decomposition of an adduct. From such conditions, it is readily seen that propagation of exothermic autodecomposition as exhibited by the controls is markedly suppressed or even entirely eliminated by the suppressor additive-containing compositions of the present invention.

The resistance to spontaneous thermal degradation of the present compositions is further substantiated by studies wherein compact masses in large packages or piles of blended mixtures are found to undergo no spontaneous heating or other evidences of adduct decomposition over prolonged periods of time at room temperature. This stability is illustrated, for example, by compositions containing either sodium bicarbonate or paraformaldehyde as the additive wherein the additive:adduct proportions on a weight basis are from about 20:80 to about 45:55.

The present compositions can be prepared using a single additive or admixture of additives. It is only essential that the resulting composition contain components that are compatible and that the additives be present in an amount sufficient to absorb the theoretical quantity of exothermic heat of reaction which would be liberated by autodecomposition of the adduct.

It is also to be understood that compositions comprising any of the hexamethylenetetramine unsaturated aliphatic halide adducts and suppressor additives as disclosed herein are within the scope of the present invention. Exemplary compositions are summarized in Table IV.

Table IV

| Composition No. | Adduct Aliphatic Halide Moiety | Weight % | Additive Type | Wt. % |
|---|---|---|---|---|
| 1 | propargyl bromide | 75 | sodium bicarbonate | 25 |
| 2 | propargyl chloride | 70 | calcium tartrate | 30 |
| 3 | diiodoacetylene | 80 | paraldehyde | 20 |
| 4 | 1,4-dichloro-2-butyne | 75 | potassium bicarbonate | 25 |
| 5 | 1,4-dichloro-2-butene | 75 | sodium bicarbonate | 25 |
| 6 | allyl chloride | 95 | paraformaldehyde | 5 |
| 7 | 2,2-dichloropropene | 80 | triuret | 20 |
| 8 | 1,2,3-trichloropropene | 85 | sodium pimelate | 15 |

I claim:
1. A substantially water-free composition consisting essentially of
   a. from about 10 to about 95 weight percent of an adduct of hexamethylenetetramine and an olefinic halide or acetylenic halide having two to eight carbon atoms, selected from the group consisting of a dihaloalkene and a haloalkyne, the halogen of which has an atomic number from 17 to 53 inclusive, and
   b. from about 90 to about 5 weight percent of a suppressor additive, said additive being a compound which undergoes an endothermic change at a temperature below that at which spontaneous exothermic decomposition of said adduct is initiated, wherein the suppressor additive is
      a. a polymeric form of formaldehyde or acetaldehyde,
      b. an alkali metal- or ammonium hydrogen carbonate,
      c. an alkali metal- or ammonium salt of a polycarboxylic lower alkylene acid having a total of 2 to 8 carbon atoms,
      d. urea,
      e. biuret or
      f. triuret.

2. The composition as defined in claim 1 having from about 55 to about 85 weight percent of the adduct and from about 45 to about 15 weight percent of the additive.

3. The composition as defined in claim 2 wherein the adduct is 1:1 hexamethylenetetramine:1,3-dichloropropene.

4. The composition as defined in claim 1 having from about 95 to about 55 weight percent of the 1:1 adduct of hexamethylenetetramine and 1,3-dichloropropene and from about 5 to about 45 weight percent sodium bicarbonate.

5. The composition as defined in claim 4 having about 75 weight percent of said adduct and about 25 weight percent sodium bicarbonate.

6. The composition as defined in claim 1 having from about 95 to about 55 weight percent of the 1:1 adduct of hexamethylenetetramine and 1,3-dichloropropene and from about 5 to about 45 weight percent paraformaldehyde.

7. The composition as defined in claim 6 having from about 95 to about 75 weight percent of said adduct and from about 5 to about 25 weight percent of paraformaldehyde.

* * * * *

UNITED STATES PATENT AND TRADEMARK OFFICE
CERTIFICATE OF CORRECTION

PATENT NO. : 4,044,007
DATED : August 23, 1977
INVENTOR(S) : William L. Howard

It is certified that error appears in the above-identified patent and that said Letters Patent are hereby corrected as shown below:

Title page, Item [57], ABSTRACT, line 9, after the word "adduct" insert the following -- is initiated prevents or markedly suppresses adduct --.

Column 3, line 67, "ahd" should read -- the --.

Column 4, line 11, "itselt" should read -- itself --.

Column 5, Table III, Run No. 3, Type "$NaCHO_3$" should read -- $NaHCO_3$ --.

Column 6, Table IV, first column heading "Composit-" should read -- Composi- --.

Signed and Sealed this

*Seventh* Day of *February 1978*

[SEAL]

Attest:

RUTH C. MASON
*Attesting Officer*

LUTRELLE F. PARKER
*Acting Commissioner of Patents and Trademarks*